United States Patent
Gagnon et al.

(10) Patent No.: US 10,259,851 B2
(45) Date of Patent: Apr. 16, 2019

(54) PROTEIN EXTRACTION METHODS

(71) Applicant: AGENCY FOR SCIENCE, TECHNOLOGY AND RESEARCH, Singapore (SG)

(72) Inventors: Peter Stanley Gagnon, Singapore (SG); Hui Theng Gan, Singapore (SG)

(73) Assignee: AGENCY FOR SCIENCE, TECHNOLOGY AND RESEARCH, Singapore (SG)

( * ) Notice: Subject to any disclaimer, the term of this patent is extended or adjusted under 35 U.S.C. 154(b) by 161 days.

(21) Appl. No.: 15/313,329

(22) PCT Filed: May 29, 2014

(86) PCT No.: PCT/SG2014/000237
§ 371 (c)(1),
(2) Date: Nov. 22, 2016

(87) PCT Pub. No.: WO2015/183183
PCT Pub. Date: Dec. 3, 2015

(65) Prior Publication Data
US 2017/0137479 A1 May 18, 2017

(51) Int. Cl.
*C07K 1/36* (2006.01)
*B01D 15/12* (2006.01)
*B01D 15/34* (2006.01)
*B01D 15/36* (2006.01)
*C07K 14/47* (2006.01)

(52) U.S. Cl.
CPC .......... *C07K 14/4702* (2013.01); *B01D 15/12* (2013.01); *B01D 15/34* (2013.01); *B01D 15/363* (2013.01); *C07K 1/36* (2013.01); *C07K 14/4703* (2013.01)

(58) Field of Classification Search
None
See application file for complete search history.

(56) References Cited

FOREIGN PATENT DOCUMENTS

WO WO2008/127305 A2 10/2008
WO WO2009/156430 A1 12/2009
WO WO2013/180648 A1 12/2013

OTHER PUBLICATIONS

Balhorn R. et al., "Mouse Sperm Chromatin Proteins: Quantitative Isolation and Partial Characterization", Biochemistry 16(18): 4074-4080 (1977). (Year: 1977).*
Extended European Search Report dated Nov. 8, 2017, for related European Patent Application No. 14893573.7.
Shechter, D., et al., "Extraction, purification and analysis of histones," Nature Protocols, vol. 2, No. 6, Jan. 2007, pp. 1445-1457.
Nian, R., et al., "Void exclusion of antibodies by grated-ligand porous particle anion exchangers," Journal of Chromatography A, vol. 1282, Mar. 1, 2013, pp. 127-132.
Chaudhuri et al, "Fractionation of chromatin nonhistone proteins," Biochim Biophys Acta, vol. 322, No. 1, Sep. 21, 1973, pp. 155-165.
Aten, R.F., et al., "A gonadotropin-releasing hormone-binding inhibitor from bovine ovaries," Purification and identification as histone H2A, J Biol Chem, vol. 264, No. 19, Jul. 5, 1989, pp. 11065-11071.
Banchev, T., et al., "Purification of histone $H1^0$ and its subfractions under non-denaturing conditions," Biochim Biophys Acta, vol. 1073, No. 1, Jan. 23, 1991, pp. 230-232.
Garcia-Ramirez, M. et al., "One-step fractionation method for isolating H1 histones from chromatin under nondenaturing conditions," Protein Expr Purif, vol. 1, No. 1, Sep. 1990, pp. 40-44.
Lindner H., et al., "Application of hydrophilic-interaction liquid chromatography to the separation of phosphorylated H1 histones,",J Chromatography A, vol. 782, No. 1, Oct. 3, 1997, pp. 55-62.
Murray K., et al., "The stepwise removal of histones from chichen erythrocye nucleoprotein," Biochem J., vol. 107, No. 2, Mar. 1968, pp. 207-215.
Written Opinion dated Aug. 28, 2017, in related Singapore Patent Application No. 11201609815Q.
Gagnon et al., "Nonspecific interactions of chromatin with immunoglobulin G and protein A, and their impact on purification performance", Journal of Chromatography A., 1340, (2014), pp. 68-78.
Nian et al., "Void exclusion of antibodies by rafted-ligand porous particle anion exchangers", Journal of Chromatography A, 1282, (2013), pp. 127-132.

* cited by examiner

*Primary Examiner* — Anand U Desai
(74) *Attorney, Agent, or Firm* — Pillsbury Winthrop Shaw Pittman, LLP

(57) ABSTRACT

Methods are provided for extracting DNA-compaction proteins from biological samples.

12 Claims, 1 Drawing Sheet

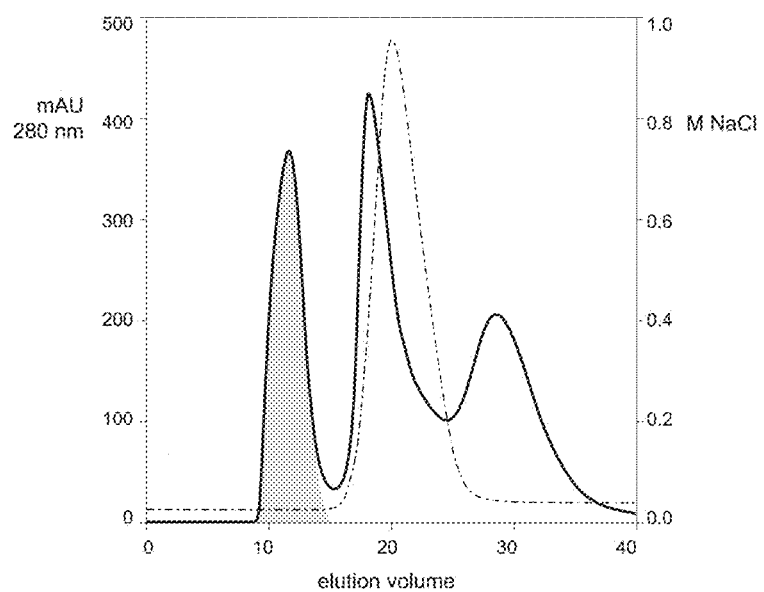

PROTEIN EXTRACTION METHODS

RELATED APPLICATIONS

This application is a U.S. National Stage of International Patent Application No. PCT/SG2014/000237, filed May 29, 2014, entitled Protein Extraction Methods, and naming inventors Peter Stanley Gagnon and Hui Theng Gan, which published as International Patent Publication No. WO/2015/183183 on Dec. 3, 2015. The entire content of the foregoing application is incorporated herein by reference, including all text, tables and drawings.

BACKGROUND

Embodiments disclosed herein relate to methods for extraction of DNA compaction proteins from protein preparations.

Methods for extraction and characterization of DNA compaction proteins have been described. One such method involves exposure of a sample to a high concentration of sodium chloride, such as 2.5 M. Another method involves exposure to low pH, such as pH 1.0 or lower for durations up to 16 hours. Combinations of sodium chloride and low pH have not been used presumably because their understood mechanisms of action are antagonistic to each other. The use of surfactants with either technique has been described along with subsequent processing by size exclusion chromatography.

SUMMARY

In some aspects, embodiments disclosed herein provide methods for extracting a DNA-compaction protein from a preparation, the method comprising contacting the preparation with an organic cation, a neutral salt, and a nonionic surfactant, at a pH of about 0.1 to about 1.0, incubating the mixture over a period of from about 30 minutes to about 150 minutes; removing solids to provide an extract, applying the extract to a particle packed column comprising (1) electropositive particles suitable for practicing anion exchange chromatography in void exclusion mode or (2) substantially uncharged size exclusion chromatography particles having an exclusion limit of about 5,000 Daltons, wherein the particle packed column has an interparticle volume, wherein a volume of the applied extract is not greater than the interparticle volume, after the applying step following with a buffer to displace the sample down the column, and collecting the extracted DNA-compaction proteins in the peak corresponding to the excluded volume of the column.

BRIEF DESCRIPTION OF THE DRAWINGS

FIG. 1 shows a chromatogram showing fractionation of the initial extract by a column of electropositive particles operated in void exclusion mode. Absorbance units (mAU at 280 nm) are shown on the left y axis, and are indicated by the solid curved line in the graph. Salt concentration of NaCl is shown on the right y-axis, and is indicated by the dotted curved line in the graph. The peak highlighted in gray contains the extracted histone proteins.

DETAILED DESCRIPTION

In some embodiments, there are provided methods for extracting DNA-compaction proteins from a biological preparation containing a desired protein, comprising an initial extraction step comprising contacting the preparation with a combination of a cationic organic compound, a neutral salt at a concentration of about 1 to about 3 M, and a nonionic surfactant, at a pH in a range from about 0.1 to about 1.0, for about 30 minutes to about two hours to provide an extract sample; then a final extraction step comprising applying the extract sample to a column packed with electropositive particles suitable for conducting fractionation in void exclusion mode, or a column packed with substantially uncharged porous particles having an exclusion limit of about 5,000 Daltons; where the volume of applied sample at the point it enters the column is less than or equal to the interparticle volume of the column; after the applying step following with a buffer to displace the sample down the column, and collecting the extracted DNA-compaction proteins in the peak corresponding to the excluded volume of the column.

In some embodiments, there are provided methods for extracting a DNA-compaction protein from a preparation, the method comprising contacting the preparation with an organic cation, a neutral salt, and a nonionic surfactant, at a pH of about 0.1 to about 1.0 incubating the mixture over a period of from about 30 minutes to about 150 minutes, removing solids to provide an extract, applying the extract to a particle packed column comprising (1) electropositive particles suitable for practicing anion exchange chromatography in void exclusion mode or (2) substantially uncharged size exclusion chromatography particles having an exclusion limit of about 5,000 Daltons, wherein the particle packed column has an interparticle volume, wherein a volume of the applied extract is not greater than the interparticle volume, after the applying step following with a buffer to displace the sample down the column, and collecting the extracted DNA-compaction proteins in the peak corresponding to the excluded volume of the column.

In some embodiments, the organic cation is selected from the group consisting of guanidinium, ethacridine, methylene blue, daunomycin, doxorubicin, chlorhexidine, alexidine, benzalkonium chloride, tris(2-aminoethyl)amine, cetyltrimethylammonium, polyethyleneimine and combinations thereof.

In some embodiments, the concentration of ethacridine or methylene blue is in a range selected from the group consisting of a non-zero amount to 0.05% (weight to volume), 0.01 to 0.1%, 0.02 to 0.05%, and 0.03 to 0.10%

In some embodiments, the concentration of guanidinium is in a range selected from the group consisting of 0.5 to 1.5 M, 0.8 to 1.2 M, and 0.9 to 1.1 M.

In some embodiments, the neutral salt is present in a concentration range from about 1 M to about 3 M.

In some embodiments, the neutral salt is sodium chloride or potassium chloride.

In some embodiments, a nonionic surfactant is selected from the group consisting of Tween 20 (polyethylene glycol sorbitan monolaurate), Tween 40 (polyoxyethylenesorbitan monopalmitate), Tween 60 (polyethylene glycol sorbitan monostearate), and Nonidet NP40 (octylphenoxypolyethoxyethanol).

In some embodiments, the nonionic surfactant is present in a concentration range from about 0.05% to about 0.25% w/v.

In some embodiments, the DNA-compaction protein comprises one or more histone proteins.

In some embodiments, the preparation is selected from the group consisting of a cell culture supernatant, a bodily fluid, a tissue homogenate, a fraction from a fractionating process.

In some embodiments, a desired non-histone protein is a naturally occurring protein or a recombinant protein.

In some embodiments, a desired non-histone protein is selected from the group consisting of an antibody, an IgG, an IgM, a non-antibody protein.

In some embodiments, a cationic organic compound may be omitted from the initial extraction step.

In some embodiments, a chromatographic final extraction step may be omitted.

In some embodiments, there are provided kits configured to carry out the methods disclosed herein.

Extraction of DNA compaction proteins is challenging because of strong self-association and interactions with DNA. While reagents for extraction are on the market, it has been discovered that methods claimed to support efficient extraction dramatically underestimate the actual amounts present. Besides apparently failing to fully liberate DNA compaction proteins such as histones from more complex structures such as nucleosomes. Known extraction conditions also degrade histones over the long course of extraction, and exacerbate the underestimation. It has been discovered that the primary mechanisms of charge suppression by high salt, and charge repulsion at low pH, employed individually by existing extraction methods, are mutually antagonistic, and when used together may create even greater underestimates of histone content, except within particular ranges. A further issue with existing histone extraction methods is that if the extraction environment is changed back to a physiological environment, the histones become undetectable in parallel, as they were in the unextracted sample. This implicates that known histone detection methods are dependent on temporary destabilization of histone-containing structures such as nucleosomes in order to expose histone antigenic sites, which indicates in turn that existing extraction methods are able to achieve exposure of those antigenic sites only while the sample resides in the extraction environment.

It has unexpectedly been discovered that host protein assays used and believed to reveal the quantity of all contaminating host proteins in preparations containing a desired recombinant protein produced by cell culture, are unable to accurately detect DNA compaction proteins, including histones. Experimental data document that host protein assays supposed to reveal total host protein underestimate histone content by more than 20,000-fold (P. Gagnon et al, J. Chromatogr. A 1340 (2014) 68-78). This represents a substantial problem in purification of biopharmaceuticals because it means that purification methods for histone removal cannot be evaluated or selected for that ability, and that final products for human therapy could contain unsafe contaminant loads.

The problem of accurate histone quantitation extends to assay calibration standards. Due to the difficulty in achieving effective extraction of histones from natural sources, some suppliers have developed cell culture processes that overexpress one species of histone so that the histones are not associated with DNA in nucleosomes. This represents an aberration itself from the composition of natural histone-containing samples, which represents a potential source of analytical error, and which is compounded by the fact that such "calibration" solutions contain only a single histone species, typically H3. It represents a further source of error to the extent that the histones expressed cytoplasmically or secreted from cells do not undergo the same post-translational modifications as natural histones.

A more effective method of histone extraction is disclosed herein, the method comprising contacting a histone-containing preparation with a combination of elements and conditions comprising a cationic organic compound, a neutral salt at a concentration of about 1 to about 3 M, a nonionic surfactant at a concentration of about 0.01 to about 0.25%, at a pH of about 0.1 to about 1.0, for 30 minutes to two hours; then applying the sample to a column packed with electropositive particles suitable for performing anion exchange chromatography in void exclusion mode, or to a column packed with substantially uncharged porous particles having an exclusion limit of about 5,000 Daltons; where the volume of applied sample at the point it enters the column is less than or equal to the interparticle volume of the column; and collecting the extracted histone proteins in the peak corresponding to the excluded volume of the column. This produces a higher recovery of histones than extraction methods that rely on pH 1, or 2.5 M NaCl, or either in combination with 0.1% of the nonionic surfactant NP40, or all of the foregoing, or guanidine by itself at any concentration. Unexpectedly, histones extracted by the disclosed method do not reassemble with DNA and other chromatin constituents upon reversion of the buffer formulation to physiological conditions. This is in fundamental contrast to known extraction methods, such as low pH alone, where restoration of a low-pH-extracted sample to physiological conditions causes the histone component to become as poorly detected as in an unextracted sample. The term "physiological conditions" is understood in the present context to refer to a pH of about 6.5 to about 7.5 and a conductivity of about 12 to about 16 millisiemens per cm (mS/cm). Without being bound by theory, it is believed that the ability of the disclosed method to avoid this limitation may result from separation of the histone-containing fraction from an as-yet-unidentified reassembly-promoting element during the final step of chromatographic separation. Where anion exchange chromatography in void exclusion mode is used as the final extraction step, it appears that residual DNA may be the primary reassembly-promoting component removed, and that it is removed by binding to the surface of the electropositive particles. Whatever the mechanism, the ability of the methods herein to prevent post-extraction reassembly permits the extracted sample to be in physiological conditions that do not interfere with subsequent immunoassays, whereas low pH extraction normally requires that the detection antibody also be applied at low pH, which may reduce signal by damaging the detection antibody or depressing its antigen-binding kinetics. A further benefit of the final chromatographic separation is that it makes it possible for extracted samples to give essentially the same results despite moderate variations in salt concentration or pH of the original sample, which is in contrast to known extraction methods such as low pH, where variations of salt concentration contribute to substantial false variation of values obtained by the subsequent assay. A further benefit of the final chromatographic separation is that it makes it possible for all extracted samples to reside in identical conditions regardless of their initial sample pH and conductivity, where uniformity of conditions among a related series of samples is understood to contribute to better overall accuracy and comparability of histone values among the samples of such a series. This benefit extends to the use of a standardized buffer for the final chromatographic separation that enables better consistency and reproducibility among samples that may be analyzed at different times, and also enables the disclosed method to be practiced in a kit format. A further benefit, achieved particularly when the chromatography media is electropositive, is that the extraction method selectively removes a large proportion of acidic contaminants that might interfere with a subsequent immunoassay. As implied, this leaves the extracted histones in a relatively purified state, demonstrating that the disclosed method can be used either for preparation of samples for quantitative assays, or for purification of calibration standards with a composition that accurately represents naturally occurring histone distributions, or for purification of samples for other purposes. A further benefit of the disclosed method, deriving from the relatively short duration of sample exposure to low pH and elevated salt concentration, is that it reduces overall assay time compared to known extraction methods such as low pH. A further benefit of the disclosed method, deriving from the relatively short duration of sample exposure to low pH and elevated salt concentration, is that it reduces damage to the extracted histones, which is a chronic problem of extraction at low pH since it also reduces the detectability of the extracted histones that causes underestimation of histone content and an increase of uncontrolled variability of results.

In one exemplary embodiment, the pH of a sample to be extracted may be reduced to about 0.1 to about 1.0 by addition of acid sufficient to achieve that condition, such as 200 mM hydrochloric acid in a volumetric proportion of about 15% v/v. Sodium chloride is added to a final concentration of 2 M. The cationic organic compound guanidine is added to a final concentration 0.25 M. The nonionic surfactant Nonidet NP40 is added to a final concentration of 0.1%, and the mixture is incubated at room temperature for 1 hour. Solids are removed by any expedient method, such as filtration or centrifugation. A column is packed with a size exclusion-based buffer exchange chromatography medium such as Sephadex G25, which is then equilibrated to 50 mM Hepes, 100 mM NaCl, pH 7.0. The clarified sample is applied to the column such that the volume of applied sample as it enters the column does not exceed the interparticle volume of the packed bed. Additional buffer is applied to the column to cause the sample to be transported through the column. The first peak, which contains the extracted histones, and which elutes in the equilibration buffer, is collected.

In another exemplary embodiment, the pH of a sample to be extracted may be reduced to about 1 by addition of acid sufficient to achieve that condition, such as 200 mM sulfuric acid in a volumetric proportion of about 15% v/v. Sodium chloride is added to a final concentration of 3 M. The cationic organic compound guanidine is added to a final concentration 0.2 M. The nonionic surfactant Tween-20 is added to a final concentration of 0.1%, and the mixture is incubated at room temperature for 1 hour. Solids are removed by any expedient method, such as filtration or centrifugation. A column is packed with an anion exchange chromatography medium such as UNOsphere Q, which is then equilibrated to 50 mM Tris, pH 8.0. The clarified sample is applied to the column such that the volume of applied sample as it enters the column does not exceed the interparticle volume of the packed bed. Additional buffer is applied to the column to cause the sample to be transported through the column. The first peak, which contains the extracted histones, and which elutes in the equilibration buffer, is collected. For example, see FIG. 1 and Example 7 below. Experimental data indicate that this approach produces higher histone recovery and a much higher level of histone purity than the approach using a column packed with nominally uncharged porous particles, both with respect to the absence of acidic proteins and the apparent absence of DNA-containing nucleosomal remnants.

In another exemplary embodiment, the pH of a sample to be extracted is reduced to about 0.1 to about 1.0 by addition of acid sufficient to achieve that condition, such as 200 mM sulfuric acid in a volumetric proportion of about 15% v/v. Sodium chloride is added to a final concentration of 1 M. The cationic organic compound ethacridine is added to a final concentration 0.025% (w/v). The nonionic surfactant NP40 is added to a final concentration of 0.1%, and the mixture is incubated at room temperature for 1 hour. Solids are removed by any expedient method, such as filtration or centrifugation. A column is packed with an anion exchange chromatography medium such as Nuvia Q, which is then equilibrated to 50 mM Hepes, pH 7.0. The clarified sample is applied to the column such that the volume of applied sample as it enters the column does not exceed the interparticle volume of the packed bed. Additional buffer is applied to the column to cause the sample to be transported through the column. The first peak, which contains the extracted histones, and which elutes in the equilibration buffer, is collected. The clarified sample is applied to the column such that the volume of applied sample as it enters the column does not exceed the interparticle volume of the packed bed. Additional buffer is applied to the column to cause the sample to be transported through the column. The first peak, which contains the extracted histones, and which elutes in the equilibration buffer, is collected.

In another exemplary embodiment, the pH of a sample to be extracted is reduced to about 0.1 to 1.0 by addition of acid sufficient to achieve that condition, such as 200 mM sulfuric acid in a volumetric proportion of about 0.8% v/v. Sodium chloride is added to a final concentration of 1.5 M. The cationic organic compound methylene blue is added to a final concentration 0.025% (w/v). The nonionic surfactant NP40 is added to a final concentration of 0.1%, and the mixture is incubated at room temperature for 1 hour. Solids are removed by any expedient method, such as filtration or centrifugation. A column is packed with an anion exchange chromatography medium such as UNOsphere Q, which is then equilibrated to 50 mM Hepes, 100 mM NaCl, pH 7.0. The clarified sample is applied to the column such that the volume of applied sample as it enters the column does not exceed the interparticle volume of the packed bed. Additional buffer is applied to the column to cause the sample to be transported through the column. The first peak, which contains the extracted histones, and which elutes in the equilibration buffer, is collected.

In some embodiments, the cationic organic compound may be chlorhexidine, benzalkonium chloride, alexidine, tris(2-aminoethyl)amine, or polyethyleneimine, or cetyltrimethylammonium bromide, or a combination of the foregoing, potentially including ethacridine, methylene blue, daunomycin, doxorubicin, and/or guanidine. Without ascribing to any particular theory, experimental data suggest that the positive charge on these compounds may enhance their interaction with the DNA component of nucleosomes and thereby competitively weaken the interaction of DNA-compaction proteins with DNA. In the case of guanidine, its extraction-enhancing effects may be further mediated by its action as a chaotrope. In the case of ethacridine, daunomycin, doxorubicin, and/or methylene blue, their extraction enhancing effects may be further mediated by their ability to intercalate into DNA structures, causing partial unwinding of the DNA, and thereby weakening the interaction of DNA and DNA-compaction proteins, such as histones.

In some embodiments, initial sample composition may be unrestricted with respect to pH, conductivity, salt species, cell culture media components, or the characteristics of the desired recombinant protein. In some embodiments, initial sample composition across a series of samples may vary systematically by one or more parameters, such as fractions from a previous adsorption chromatography purification step, that may vary from one to another by an increase or decrease of salt content, or pH, or other parameter, as well as each potentially containing a different subset of proteins. In some embodiments, initial sample composition among a series of samples may vary with respect to the subset of proteins present from one sample to the next, but the conditions may be virtually invariant, for example when the samples were derived from a size exclusion chromatography step.

In some embodiments, the buffer used for the chromatography step may also be the buffer in which the final extracted sample resides. In some such embodiments, the final buffer may contain only a buffering component and lack additional salts or other components, such as preservatives or cryoprotectants, among others. In some such embodiments, the final buffer conditions may reasonably simulate physiological conditions. In some such embodiments, the same buffer may be used to process all of the samples in a related set. In some such embodiments, the same buffer may be used to process all of the samples across unrelated sets.

In some embodiments, the initial extraction pH may be about 0.1 to 1.0. In some such embodiments, the extraction pH is achieved by addition to the sample of 200 mM hydrochloric acid, or sulfuric acid, or other acid, or combination of acids. In some such embodiments, the extraction pH is achieved by addition to the sample of about 200 mM acid in a proportion of 15% v/v. In some embodiments, the volumetric proportion of added acid may be 5 to 50%, or 10 to 25%, or 12.5 to 17.5%. In some embodiments, the concentration of acid may be 100 mM, or 200 mM, or 300 mM, or a lower, intermediate or higher concentration. In some such embodiments, the volume and concentration of the acid will be adjusted to the lowest amount of acid that achieves the target pH. In some embodiments, the target pH may be in a range from 0.1 to 1.0, or from 0.2 and 0.9, or from 0.3 and 0.8, or from 0.4 and 0.7, or from 0.5 and 0.6, or a different range or intermediate value. In some embodiments, another acid or combination of acids may be employed at a similar overall concentration, or at a higher concentration if necessary to overcome buffering effects of the sample, or lower if shown to achieve the target pH, or at a different proportion.

In some embodiments, the concentration of a neutral salt during the extraction may be 1 M, or 2 M, or 3 M, or in a range from 1 M and 3 M, or from 1.5 M and 2.5 M, or from 1.75 and 2.25 M, or from 1.8 and 2.2 M, or from 1.9 and 2.1 M, or a different range or intermediate value. In some such embodiments, the neutral salt will be NaCl or KCl, or a combination thereof, or other neutral salt. In some embodiments, the salt may be added as a liquid concentrate. In some embodiments, the neutral salt may be added as a solid.

In some embodiments, the cationic organic compound may be a guanidinium ion, added either as a free base or as a salt, such as guanidine sulfate, or guanidine hydrochloride, or guanidinium acetate. In some such embodiments, the concentration of guanidinium ions in the final extraction mixture will be a nonzero amount less than 2 M. In some such embodiments, the concentration may be 0.05 M, or 0.1 M, or 0.15 M, or 0.2 M, or 0.25 M, or 0.5 M, or 1.0 M, or 1.5 M. In some such embodiments, the guanidinium concentration may be in a range from 1.5 M and 0.05 M, or from 1 M and 0.1 M, or from 0.5 M and 0.15 M, or from 0.4 and 0.2 M, or a different range or intermediate concentration. In some embodiments, the cationic chaotrope may be added as a liquid concentrate. In some embodiments the cationic chaotrope may be added as a solid. In some embodiments, guanidinium ions may be absent.

In some embodiments, the cationic organic compound may be ethacridine or methylene blue, at a concentration of 0.025% (w/v), or 0.01%, or 0.1%, or a concentration from 0.01 and 0.1%, or an intermediate value.

In some embodiments, the nonionic surfactant may be Nonidet NP40, or Tween-20, or Tween-40, or Tween-60. In some such embodiments, the surfactant concentration may be 0.01%, or 0.025%, or 0.05%, or 0.075%, or 0.1%, or 0.25%, or 0.5%, or in a range from 1% and 0.01%, or from 0.5% and 0.05%, or from 0.25% and 0.025%, or from 0.2% and 0.02%, or from 0.15% and 0.05%, or from 0.125% and 0.075%, or from 1.1% and 0.9%, or a different range or intermediate value. In some embodiments, the nonionic surfactant may be a species other than NP40 or Tween, such as Triton, or Brij, or other species. In some embodiments, the nonionic surfactant may be replaced by a zwitterionic surfactant, such as CHAPS, CHAPSO, or octaglucoside. In some embodiments, the nonionic surfactant may be replaced by an anionic surfactant such as cetyltrimethylammonium bromide.

In some embodiments, the period of initial extraction may be 15 minutes, or 30 minutes, or 60 minutes, or 120 minutes, or 150 minutes, or 180 minutes, or longer. Experimental data suggest that degradation of histones occurs at intervals greater than 1 hour, but is still fairly minor at two hours, though more severe at longer intervals. An interval of 30 minutes tends to result in lower apparent values than 60 minutes, suggesting 1 hour as a reasonable minimum extraction period, but leaving the possibility that an intermediate duration might be preferred in some cases. In some such embodiments, it may be prudent to evaluate a range from 30 minutes and 150 minutes, or from 45 minutes and 90 minutes, or from 50 minutes and 70 minutes, or other interval or intermediate value. Data indicate that sample composition may influence the most effective duration, and that samples which have contained dead cells for the longest period are most likely to require the longest acid-exposure intervals since they will represent situations where a desired protein product will have had the greatest opportunity to interact with extracellular chromatin, potentially leading to formation of aggregates that resist dissociation.

In some embodiments, the chromatography media used for the final step of the extraction may comprise electropositive porous particles such as used to practice the technique of anion exchange chromatography. In some such embodiments, the anion exchange media may be particular chosen according to their known ability to support the technique of anion exchange chromatography in void exclusion mode, as described by R. Nian et al (J. Chromatography A 1282 (2013) 127-132). In some such embodiments, the anion exchange medium may be UNOsphere Q (Bio-Rad Laboratories). In some such embodiments, the anion exchange medium may be Nuvia Q (Bio-Rad Laboratories). In some such embodiments, the anion exchange medium may be Capto Q (GE Healthcare), or another anion exchanger suitable to practice the technique. In some embodiments the volume of the sample as it enters the column will be less than the interparticle volume of the column. In some such embodiments, the volume of the sample may be 1% less than the interparticle volume of the column. In some such embodiments, the volume of the sample may be 5% less than the interparticle volume, or 10% less, or 20% less, or 50% less, or 90% less, or 99% less, or any reduction to a sample volume smaller than a non-zero amount, but sample volume should generally not exceed the interparticle volume.

In some embodiments where an anion exchange medium in void exclusion mode is used for the final extraction step, the equilibration buffer selected to perform this step may benefit by embodying an alkaline pH at the lowest conductivity where a desired non-histone protein, if present, remains soluble and unretained by the anion exchange medium. In some embodiments where an anion exchange medium in void exclusion mode is used to purify histones for use as calibrations standards, or for other purposes, and no desired non-histone protein is present, it may be beneficial to employ an alkaline pH at the lowest conductivity at which histones remain stable and unretained by the anion exchange medium. Accordingly, the pH may be 8.0, or 9.0 or 9.5, or 10.0, or higher. In some such embodiments salts will be absent. In some such embodiments, the buffering species may be selected so as to impart the lowest conductivity to the buffer. For example, zwitterionic buffers typically impart negligible conductivity to a buffer themselves, and any conductivity present is attributable to the counterions used to adjust their pH. It will be apparent to the person of skill in the art that the higher the pH and lower the conductivity, the larger the diversity of acidic species that will be removed from the sample coincident with extraction of histone proteins. It will be equally apparent that these conditions will be most likely to remove DNA-containing nucleosomal remnants since they will favor DNA binding to the electropositive surface of the exchanger while minimizing charge repulsion by the histone component. In other words, such conditions will yield the highest histone purity, especially with respect to removal of DNA. This may be expected to be advantageous where the objective is to obtain highly purified histones for use as calibration standards, or to obtain purified histones so that they can be characterized. It will be known to persons of skill in the art how to scale up the extraction technique to obtain purified histones in whatever quantities desired.

In some embodiments, the chromatography media used for the final step of the extraction may comprise size exclusion chromatography particles such as used to practice the technique of buffer exchange chromatography. In some such embodiments, the buffer exchange medium may embody an exclusion limit corresponding to a hypothetical globular protein with a mass of about 5,000 D. In some such embodiments, the buffer exchange media may be Sephadex G25. In some such embodiments, the particle size distribution of the media be altered by particle sizing performed by the manufacturer, where with Sephadex G25 for example, the smallest particle size distribution will be associated with the grade of G25 known as superfine, and a lightly larger particle size distribution will be associated with the grade of G25 known as fine, and a slightly higher particle size distribution will be associated with the grade of G25 known as medium, and a slightly higher particle size distribution will be associated with the grade of G25 known as coarse. In some embodiments, porous particles with an exclusion limit of about 5,000 D may be constructed from other polymers, for example Trisacryl GF05, which is understood to be made from an acrylamide polymer, versus the dextran polymer used for Sephadex. In some embodiments, higher histone recovery may be achieved with size exclusion media with a lower exclusion limit, such as Sephadex G10. As a general matter, the capacity and quality of fractionation offered by such media will be highest with the grade corresponding to the smallest and narrowest particle size distribution. In some embodiments the volume of the sample as it enters the column will be less than the interparticle volume of the column. In some such embodiments, the volume of the sample may be 1% less than the interparticle volume of the column. In some such embodiments, the volume of the sample may be 5% less than the interparticle volume, or 10% less, or 20% less, or 50% less, or 90% less, or 99% less, or any reduction to a smaller non-zero amount.

In some embodiments where a size exclusion medium is used for the final extraction step, the equilibration buffer selected to perform this step may embody a wide range of conditions without reducing overall histone extraction efficiency. The pH may range from 4 to 10, conductivity can range from less than 1 mS/cm to 50 mS/cm or more, and the buffer may contain surfactants or other additives.

In some embodiments where the final extraction step is performed with either an electropositive chromatography medium or with a size exclusion chromatography medium, and the purpose of performing the disclosed methods is used to prepare samples for quantitative analysis of histones, the buffer selected to equilibrate the column step will be formulated accommodate the needs of a follow-on immunoassay. It will be understood by persons of skill in the art that immunoassays employing different sensors require different chemical environments to achieve optimal performance, and the ability of the disclosed methods to accommodate these needs thereby increases their flexibility and scope of application. In some embodiments, for example where the disclosed methods are used to extract histones as calibration standards, the buffer chosen for the final extraction step may be chosen to be histone-stabilizing buffer, and/or may be formulated especially during storage under refrigerated or freezing conditions.

DEFINITIONS

Terms are defined so that the embodiments herein may be understood more readily. Additional definitions are set forth throughout the detailed description.

"DNA compaction protein" refers to a species of protein that interacts with genomic DNA in such a way as to allow long segments of DNA to reside within a small area by virtue of it being folded, coiled, or supercoiled as a result of its interactions with one or more species of DNA compaction proteins.

"Histone" refers to a group of species of DNA compaction proteins found in eukaryotic organism. Histones are generally of 5 species, consisting of histone H1, H2A, H2B, H3, and H4.

"Nucleosome" refers to a secondary structure created by the interaction of DNA compaction proteins with DNA, whereby the secondary structure mediates the compaction of DNA. Nucleosomes generally consist of a core histone octamer comprising 2 each of histones H2A, H2B, H3, and H4, where DNA is wrapped about 1.5 times around the core. The association of histones with DNA within a nucleosome are so strong that they stabilize both the DNA and the histone components from lysis, dissociation, or conformational change, leading to the requirement for a chemically severe extraction procedure to make the histones detectable to immunoassays.

"Nucleosome array" refers to 2 or more nucleosomes linked in a linear arrangement by a section of linker DNA that is itself associated with histone H1.

"Chromatin" refers to genomic DNA and the associated DNA compaction proteins and other constituents. Chromatin begins to degrade immediately upon cell death, leading to the formation of nucleosomal arrays of varying sizes, single nucleosomes, histones, and DNA.

"Interparticle volume" refers to the space from particles packed in a 3-dimensional space, such as a chromatography column. The interparticle volume is more commonly referred to the void volume of a column, or the column void, or simply the void. The term interparticle volume is considered the most precise because void volume is sometimes used to refer to the deep internal volume of a particle, to which proteins never achieve access due to the inefficiency of diffusive mass transport, or to the pores simply being shallow. In a typical system, the void volume in a column of gravity-settled particles constitutes about 40% of the total bed volume.

"Exclusion limit" refers to the size of the largest protein that can enter the pores of a porous particle-based chromatography medium. This is understood to be an arbitrary guideline based on a hypothetical globular (spherical) protein. For example, a chromatography medium with an exclusion limit of 5,000 D would permit proteins smaller than 5,000 D to diffuse into its pores, while proteins larger than 5,000 D would not be able to diffuse into such pores. Naturally occurring proteins are understood not to be perfectly spherical, so this example is understood to be unrealistically stringent, however the exclusion limits published by media manufacturers can be useful to identify candidate media for rough size classes of molecules.

"Void exclusion" as it applies to nominally uncharged porous particles such as used for size exclusion chromatography refers to the phenomenon whereby proteins and/or other solutes larger than the exclusion limit are restricted by their size to the interparticle volume of a column. "Void exclusion" as it applies to electropositive particles refers to the phenomenon whereby a subset of proteins and or other solutes are restricted to the interparticle volume of a column by their charge properties. Detailed discussion of void exclusion in columns of electropositive particles is provided by Nian et al (supra). In the cases of both void exclusion by size and by charge, column loading is similarly restricted to a sample volume not greater than the interparticle volume of a column; and in both cases, the first peak eluting from the column is understood to contain the components of the original sample that were excluded into the interparticle volume (the void volume) during their passage through the column. This peak is commonly referred to as the void peak, void exclusion peak, or exclusion peak.

"Cationic" refers to an ion that is positively charged.
"Anionic" refers to an ion that is negatively charged.
"Nonionic" refers to an ion that lacks charge.
"Zwitterionic" refers to a compound that bears both positive and negative charges in a balance whereby the positive charge cancels out the effect of the positive, and vice versa, so that the net charge on the compound is zero.

"Chaotrope" refers to a compound that tends to denature proteins or other biomolecules, where the term denature is understood to mean relax the structure to a degree where a protein loses its natural function and, where taken to an extreme, may completely lose recognizable structural features. Commonly known chaotropes include guanidinium ions (cationic), urea (nonionic), and thiocyanates (anionic).

In certain embodiments, the disclosed method can be applied without variation from the general examples described above to obtain good quantitative estimates of the histone content of a given sample. As a general matter, the second phase of the extraction, involving the chromatographic step, should be initially conducted with a column of electropositive porous particles since experimental data show that they support the highest histone recovery and purity. Given the potential for original unextracted samples to vary with respect to the composition of histone-containing entities originally present in a sample, it may be prudent to check certain variables to make sure that the conditions are appropriately matched to sample. For example, in samples derived by homogenization of living cells, the histones will be associated almost exclusively with nucleosomes. Such samples may be preferred for preparation of calibration standards. In samples derived from biological fluids containing dead cells, nucleosomes and their degradation byproducts have been shown experimentally to become associated with other proteins produced by cells (P. Gagnon et al, supra), which may make the histones more resistant to extraction; or a subset of the total histone population may be free of encumberments due to enzymatic lysis of previously-associated DNA, potentially leaving them more vulnerable to degradation. In some embodiments, the characteristics of the desired recombinant protein may be of a nature to mediate strong interactions with histones or nucleosomal structures that may also affect their extractability. The simplest process variable to check will be extraction time. Experimental data to date indicate that extraction efficiency increases up to about 60 minutes, then appears to go down if continued for longer intervals. The reduction is understood not to reflect extraction efficiency but rather the degradation of histones due to excessive exposure to extraction conditions. Whatever the cause, a simple experiment evaluating different extraction times may be performed to determine the optimum for samples from a given source. Other variables may also be optimized in a similar conceptual manner, where the concentration of neutral salt, organic cation, or surfactant, or pH, or combinations are systematically varied. In some embodiments, it is also possible to test different species of neutral salts, acids, chaotropes (cationic, non-ionic, zwtterionic, anionic), DNA intercalating agents, and surfactants. The technique known as Design of Experiments (DoE) is widely known in the art for minimizing the number of tests required to obtain a statistically valid body of data to identify the optimum conditions for a given set of variables.

In some embodiments, it will be advantageous to begin using a final extraction step that uses a column packed with electropositive particles in void exclusion mode, since this usually produces the highest recovery and the highest purity of histones. In some embodiments, it may be worthwhile to evaluate the results achieved by using size exclusion chromatography for the final step, versus anion exchange chromatography for the final step. In some embodiments, it may be worthwhile to evaluate different grades or types of size exclusion media, or different anion exchange chromatography media to determine which mediates the highest degree of overall extraction efficiency.

In some embodiments, when using a previously uncharacterized anti-histone ELISA for analysis, it may be useful to test a guanidine-based extraction versus an ethacridine or methylene blue-based extraction, since experimental data indicate that the different antibodies used by different ELISA products may be less or better able to detect histones detected from samples prepared by one or the other extraction method. In some embodiments however, extraction with an organic cation such as ethacridine, methylene blue, daunomycin, doxorubicin, or other DNA intercalator will generally support the highest recovery of extracted histones, especially when followed by application to a column of electropositive particles suitable for conducting anion exchange chromatography in void exclusion mode.

Some chromatography media suitable for conducting the final extraction step are known, but not all have been surveyed, and new media may be developed that prove to be suitable for practicing the disclosed methods. Size exclusion chromatography media known to be suitable include Sephadex G25, preferably of superfine or fine grade, but medium and coarse grades can also support a satisfactory result, as may products such as Trisacryl GF05. Anion exchange chromatography media known to be suitable include UNOsphere Q, Nuvia Q, and Capto Q, with UNOsphere Q having produced particularly excellent results. In some embodiments, it will be necessary to determine the volume of sample that may be applied to a given column packed with a given chromatography medium. This can be determined for both media classes in a simple experiment where a preparation of lysozyme at 1 mg/mL in 50 mM sodium phosphate, 1 M NaCl at pH ~7.0 is applied to a packed column equilibrated to 50 mM sodium phosphate, pH 7.0. On a first pass, make a chart mark to indicate the point at which sample is applied, and apply a sample volume of 10% the volume of the column. Follow sample introduction with equilibration buffer to displace the sample components down the column. Monitor absorbance of ultraviolet light at 280 nm, and conductivity. On the elution profile, mark the point at which the 280 signal begins to ascend, then mark the point at which the conductivity signal begins to ascend. The volume from these two points is a function of the interparticle (void) volume of that column, and provides an estimate of the maximum volume of sample that may be applied to that column in order for the histones in entire void peak to be extracted as fully as possible. In a subsequent experiment, load 20% of the column volume. In a subsequent experiment load 30% of the column volume. In each case check to make sure that the UV absorbance returns to baseline before the conductivity signal begins to increase. The objective is to identify the maximum sample volume that fulfills this condition. In a column packed with perfectly spherical particles of uniform diameter, the interparticle volume is close to 40% of the column volume, but it may be of a lesser proportion depending on a variety of factors (Nian et al supra). For example, practical experience demonstrates that compression of the column during packing differentially reduces interparticle volume. In addition, uncontrolled fluid dispersion from the point where the sample is introduced into the system and where it actually enters the column can result in the volume of sample entering the column being larger than the volume that was introduced through an injection port. For these reason, it may be prudent to run a simple experiment where samples of various volumes are introduced as described above, to determine the largest volume of sample that can be introduced at the sample port and still provide for the desired histone-extracted peak to elute completely before the salts and other components elute.

In some embodiments, it may be of interest to evaluate chaotropic compounds other than cationic organic compounds, though experimental data to date indicate that alternatives are inferior. Urea is a well-known chaotropic agent that fails to give results comparable to guanidinium ions. This result was unexpected since both guanidinium ions and urea are both known to mediate their chaotropic effects by direct binding to biomolecules, and both should have similar effects with respect to damaging histones. Without ascribing to any particular theory, it may be that the electropositive guanidinium ions are electrostatically repelled to some degree from electropositive histones, which thereby tolerate a higher concentration of guanidine than they might if guanidine was not repelled. At the same time, guanidinium ions may preferentially denature DNA by electrostatically binding of positively charged guanidinium ions to negatively charged oxygen atoms at each phosphodiester bridge on DNA, and that denaturation might help to dissociate histones from DNA, thereby contributing to higher extraction efficiency. Anionic chaotropes such as thiocyanates or perchlorates may also be considered, though preliminary data indicate that they are also inferior to guanidinium.

In some embodiments, cationic organic compounds other than guanidine may improve histone extraction efficiency, such as ethacridine and methylene blue. Experimental data indicate that other cationic organic compounds support more complete extraction than systems lacking cation organic compounds, though they are generally not as effective as ethacridine or methylene blue. In some such embodiments, the alternatives to ethacridine or methylene blue may consist of chlorhexidine, alexidine, cetyltrimethylammonium, daunomycin, doxorubicin, tris(2-aminoethyl)amine, and/or polyethyleneimine.

EXAMPLES

Example 1

Impact of different detergents and concentrations. A series of experiments was conducted to evaluate the effects of different detergents on histone extraction in 2.5 M NaCl, 0.2 M HCl. All detergent concentrations were 0.05%. Extraction efficiency was based on an ELISA obtained from Active Motif (Tokyo). The highest extraction efficiencies were obtained with Tween-20, Tween-40, Tween-60, and Nonidet NP-40. Complete data are shown in Table 1:

TABLE 1

| Surfactant | Histone H3, ng/mL |
|---|---|
| Ethylenediamine tetrakis tetrol | 0 |
| Cholaminopropyldimethylammonium propane sulfonate | 37 |
| Tween-65 | 50 |
| Decyltrimethylammonium bromide | 98 |
| No surfactant | 101 |
| Hexadecyltrimethylammonium bromide | 283 |
| Myristyltrimethylamine bromide | 351 |
| Trimethyloctadecylammonium bromide | 386 |
| Pluronic F126 | 567 |
| Glycholic acid ethoxylate | 678 |
| Dodecyltrimethylammonium bromide | 703 |
| Tween-60 | 865 |
| Tween-40 | 888 |
| Tween-20 | 890 |
| Nonidet NP40 | 939 |

Example 2

Effect of surfactant concentration across different detergents. The highest performing detergents from Example 2 were compared at different concentrations with ELISAs obtained from Active Motif, Inc and Cell Signaling (Danvers, Mass., USA). Extraction was performed in 2 M NaCl, 0.2 M HCl. The extract was buffer exchanged with a column of Sephadex G25 (GE Healthcare) into 50 mM Hepes, 150 mM NaCl, pH 7. Tween-20 provided particularly good results. Complete data are shown in Table 2:

TABLE 2

| Surfactant | H3/Active Motif | H3/Cell Signaling |
|---|---|---|
| None | 92 | 0 |
| Nonidet NP40 | | |
| 0.01% | 650 | 206 |
| 0.05% | 4203 | 509 |
| 0.10% | 4704 | 404 |
| 0.15% | 4755 | 316 |
| 0.20% | 4937 | 181 |
| Tween-20 | | |
| 0.01% | 1736 | 0 |
| 0.05% | 6478 | 748 |
| 0.10% | 6333 | 844 |
| 0.15% | 6984 | 957 |
| 0.20% | 6376 | 769 |
| Tween-40 | | |
| 0.01% | 1783 | 0 |
| 0.05% | 4678 | 270 |
| 0.10% | 5438 | 443 |
| 0.15% | 4760 | 28 |
| 0.20% | 5160 | 249 |
| Tween-60 | | |
| 0.01% | 2648 | 0 |
| 0.05% | 4039 | 235 |
| 0.10% | 4620 | 234 |
| 0.15% | 4457 | 87 |
| 0.20% | 4383 | 74 |

Example 3

Effect of extraction time on quantitation of histone H3. A sample of cell culture media containing a monoclonal antibody was extracted in 0.2 M HCl, 0.1% NP-40, 2,5 M NaCl, at 4 degrees C. Aliquots were removed at regular time intervals, and buffer exchanged on Sephadex G25 into 50 mM Hepes, 150 mM NaCl, pH 7.0. Histone H3 values were determined with an ELISA manufactured by Cell Signaling. Signal was reduced about 15% over a 16 hour (960 min) time course. Results are shown in Table 3:

TABLE 3

| Time interval (min) | Histone H3 |
|---|---|
| 0 | 3 |
| 30 | 2778 |
| 60 | 2774 |
| 120 | 2665 |
| 240 | 2484 |
| 360 | 2590 |
| 480 | 2449 |
| 960 | 2366 |

Example 4

Effects of different organic cations in 2 M NaCl, 0.2 M HCl, 0.1% NP40. Samples buffer exchanged into 50 mM Hepes pH 7.0 after initial extraction. Selected non-cationic organic compounds were also evaluated. Histone H3 values determined with ELISAs from Active Motifs and Cell Signaling. Ethacridine gave the particularly good results with Activ Motif ELISA. Guanidine gave particularly good results with the Cell Signaling ELISA. All cationic organic compounds were superior to non-cationic organic compounds. Results are shown in Table 4:

TABLE 4

| Organic cation | H3/Active Motif | H3/Cell Signaling |
|---|---|---|
| Chlorhexidine | | |
| 0.001% | 2056 | 517 |
| 0.01% | 1840 | 515 |
| Ethacridine | | |
| 0.025% | 2961 | 480 |
| 0.05% | 3663 | 371 |
| Cetyltrimethylammonium bromide | | |
| 0.025% | 1367 | 0 |
| 0.050% | 1540 | 0 |
| Polyethyleneimine-1200 | | |
| 0.025% | 2839 | 583 |
| 0.05% | 2968 | 642 |
| Guanidine | | |
| 0.5M | 311 | 717 |
| 1.0M | 504 | 1319 |
| 1.5M | 1323 | 1578 |
| 2.0M | 2438 | 841 |
| 2.5M | 3487 | 0 |
| Non-cationic organics | | |
| Urea | | |
| 1.5M | 1415 | 947 |
| 2.0M | 842 | 997 |
| 2.5M | 655 | 916 |
| Sodium thiocyanate | | |
| 0.25M | 0 | 0 |
| 0.50M | 0 | 0 |
| 1.0M | 0 | 0 |
| 1.5M | 0 | 0 |

Example 5

Comparison of ethacridine, methylene blue, and guanidine, 1.5 M NaCl, 0.1% NP-40, 0.2 M HCl. Buffer exchanged into 50 mM Hepes, pH 7.0 with Sephadex G25. Histone H3 measured by ELISA, experiments run in triplicate and results averaged. Results are shown in Table 5:

TABLE 5

| Organic cation | H3/Active Motif | H3/Cell Signaling |
|---|---|---|
| Ethacridine | | |
| 0.025% | 3236 | 2714 |
| 0.050% | 2936 | 2736 |
| 0.100% | 2768 | 3009 |
| 0.150% | 2688 | 3278 |
| 0.200% | 3122 | 3479 |
| Methylene blue | | |
| 0.025% | 2064 | 3638 |
| 0.050% | 2331 | 3479 |
| 0.100% | 4065 | 3196 |
| 0.150% | 3468 | 3259 |
| 0.200% | 3248 | 3166 |
| Guanidine | | |
| 0.5M | 1031 | 4149 |
| 1.0M | 559 | 3980 |
| 1.5M | 524 | 1529 |
| 2.0M | 550 | 384 |
| 2.5M | 444 | 171 |

Example 6

Comparison different extraction methods. A variety of extraction methods were compared and the extracted samples evaluated with ELISAs from Active Motifs and Cell Signaling. Extraction 1: no extraction, experimental control. Extractions 2: 0.2M HCl. Extraction 3: 0.2M HCl, titrated subsequently to pH 7.0. Extraction 4: 0.2M HCl, buffer exchanged by size exclusion into 50 mM Hepes, pH 7.0. Extraction 5: 2.5 M NaCl, 0.1% NP40. Extraction 6: 2.5 M NaCl, 0.1% NP40, buffer exchanged by size exclusion into 50 mM Hepes, pH 7. Extraction 7: 0.2M HCl, 1.5M NaCl, 0.1% NP40. Extraction 8: 0.2M HCl, 1.5M NaCl, 0.1% NP40, buffer exchanged by size exclusion into 50 mM Hepes, pH 7. Extraction 9: 0.2M HCl, 2M NaCl, 0.1% NP40, 1.25 M guanidine HCl. Extraction 10: 0.2M HCl, 2M NaCl, 0.1% NP40, 1.25 M guanidine HCl, then buffer exchange by size exclusion into 50 mM Hepes, pH 7. Extraction 11: 0.2M HCl, 1.5 M NaCl, 0.1% NP40, 0.2% ethacridine. Extraction 12: 0.2M HCl, 1.5 M NaCl, 0.1% NP40, 0.2% ethacridine, then buffer exchange by size exclusion chromatography into 50 mM Hepes, pH 7. Results are shown in Table 6:

TABLE 6

| Extraction Method | Cell Signaling | Active Motif |
|---|---|---|
| 1 | 26 | 0 |
| 2 | 2245 | 655 |
| 3 | 585 | 175 |
| 4 | 14 | 0 |
| 5 | 2241 | 1206 |
| 6 | 837 | 185 |
| 7 | 139 | 761 |
| 8 | 3636 | 4580 |
| 9 | 89 | 375 |
| 10 | 5884 | 2755 |
| 11 | 126 | 728 |
| 12 | 4337 | 5948 |

Example 7

Second extraction step with void exclusion anion exchange versus size exclusion. Cell culture harvest containing an IgG monoclonal antibody was extracted with 0.2 M HCl, 2 M NaCl, 0.1% NP40, 0.05% ethacridine, for 1 hour. Half of the sample was processed by a final extraction step of buffer exchange chromatography into 50 mM Tris, pH 8 on Sephadex G25. The other half was processed by void exclusion chromatography into 50 mM tris, pH 8 on UNOsphere Q. The samples were assayed with histone H3 ELISAs from Active Motifs and Cell Signaling. Average H3 values for the void exclusion peak on both columns are given in the following table. Void exclusion anion exchange chromatography gave the highest response with both assays. Results are show in Table 7:

TABLE 7

| Final extraction | Active Motif | Cell Signaling |
|---|---|---|
| Void exclusion | 3343 | 1000 |
| Size exclusion | 337 | 310 |

FIG. 1 illustrates the step employing void exclusion anion exchange chromatography and highlights the collected void exclusion peak in gray.

Example 8

Formation of precipitates following final extraction. When the initial extraction is performed at concentrations of NaCl lower than 0.5 M, precipitation is observed following buffer exchange by size exclusion chromatography into 50 mM Hepes pH 7.0. A similar result is observed if initial extraction is performed in the absence of guanidine, even in 1 M NaCl. A similar result is observed if the initial extraction is performed in greater than 0.75 M guanidine in the presence of 1 M NaCl. A similar result is observed in 0.0 to 0.5 M NaCL, when initial extraction is conducted in the presence of ethacridine or methylene blue. In all cases, removal of the precipitate corresponds directly to a loss of H3 signal, indicating that the precipitate is populated by histone proteins.

It will be apparent from the above examples that the disclosed methods achieve a higher degree of histone extraction efficiency than known methods, even in the absence of the cationic organic compound. Given the intent of the disclosed methods to support the most accurate quantitation of histone proteins in a given sample, the inclusion of the cationic organic compound is to be preferred, though it is recognized that some users may judge acceptable results can be obtained without it. Even in such cases however, the person of skill in the art will recognize that inclusion of the chromatography step will remain necessary. It should be equally recognized that the addition of the chromatography steps described as part of the disclosed method, to known extraction methods, will confer some of the advantages of the disclosed methods to those other methods.

In some embodiments, the disclosed methods may be used to extract histones from samples for the purpose of developing a quantitative estimate of the histones within those samples. Thus, in some embodiments, methods disclosed herein may further comprise the step of quantifying the amount of histones in a sample or preparation or the like. Such samples or preparations may comprise bodily fluids, cell or tissue lysates, cell culture supernatants, and samples processed from any such sources, such as from purification processes. In some embodiments, the methods may further comprise the step of comparing the quantified amount of histones to a reference quantity of histones or an internal standard. The purpose of developing a quantitative estimate may be to determine the quantity of histones in a desired purified therapeutic protein intended for human injection, to be sure that the desired protein meets appropriate safety and regulatory standards. In some embodiments, after quantifying the amount of histones, the methods may include a step of determining whether the amount of histones meets a safety and/or regulatory standard. In another such embodiment, the purpose of developing a quantitative estimate may be to determine the quantity of histones in each of a series of fractions collected from a fractionation (purification) step intended to remove histones and/or other contaminants.

In some applications, the purpose of developing a quantitative estimate may be to determine the quantity of histones remaining after each of a series of fractionation steps. In such embodiments, the purpose of developing a quantitative estimate may be to guide the development of fractionation methods intended specifically to remove histones from a preparation by a candidate process. Thus, in some embodiments, methods disclosed herein may further comprise the step of quantifying the amount of histones in one or more fractions or similarly divided group of histone sources. After quantifying histones in a series of fractions, the methods may further comprise collecting all fractions comprising histone. After collecting all fractions, the histones may be further subject to one or more steps of isolating the histones, buffer exchanging the collected fractions, filtering, micro- or nanofiltering, further purifying via a chromatography method, or combinations thereof In some embodiments, the disclosed methods may be used to extract histones for the purpose of creating a calibration standard to support quantitative analysis of histones in samples comprising unknown histone contents. Thus, in some embodiments, methods disclosed herein may further comprise the step of forming a calibration standard with the extracted histone. In some embodiments, the sample from which the histones are extracted may be a living cell preparation. Thus, methods may include a first extraction step of the methods disclosed herein may be with a living cell preparation. In other embodiments, the sample from which the histones are extracted may be a cell culture medium such as used in the production of recombinant proteins, and may contain a significant proportion or dead cells. In other such cases, the sample from which the histones are detected may be a bodily fluid, such as serum, or plasma, or tears, or breast milk, or pleural fluid, or saliva or other bodily fluid. In other embodiments, the disclosed methods may be used to extract histones for the purpose of purifying them. In some such embodiments, particularly where the final extraction step is performed with a column of electropositive particles used in void exclusion mode, substantial purification of histones will occur coincident with extraction. In some such embodiments, the partially purified histone extract produced by the disclosed methods may be further purified by other methods. In some embodiments, such other methods may include chromatography methods such as one or more of the following: hydrophobic interaction chromatography, cation exchange chromatography, hydroxyapatite chromatography, mixed mode chromatography, affinity chromatography, size exclusion chromatography.

All references cited herein are incorporated by reference in their entirety and for all purposes to the same extent as if each individual publication or patent or patent application was specifically and individually indicated to be incorporated by reference in its entirety for all purposes. To the extent publications and patents or patent applications incorporated by reference contradict the disclosure contained in the specification, the specification is intended to supersede and/or take precedence over any such contradictory material.

All numbers expressing quantities of ingredients, chromatography conditions, and so forth used in the specification and claims are to be understood as being modified in all instances by the term "about." Accordingly, unless indicated to the contrary, the numerical parameters set forth in the specification and attached claims are approximations that may vary depending upon the desired performance sought to be obtained by the present embodiments.

Many modifications and variations of the embodiments disclosed herein can be made without departing from its spirit and scope, as will be apparent to those skilled in the art. The specific embodiments described herein are offered by way of example only and are not meant to be limiting in any way. It is intended that the specification and examples be considered as exemplary only, with the true scope and spirit of the embodiments herein being indicated by the following claims.

What is claimed is:

1. A method for extracting a DNA-compaction protein from a preparation, the method comprising:

(i) contacting a preparation comprising DNA-compaction proteins with an organic cation, a neutral salt, and a nonionic surfactant, at a pH of about 0.1 to about 1.0;
(ii) incubating the mixture over a period of from about 15 minutes to about 150 minutes;
(iii) removing solids to provide an extract;
(iv) applying the extract to a particle packed column comprising (1) electropositive particles suitable for practicing anion exchange chromatography in void exclusion mode or (2) substantially uncharged size exclusion chromatography particles having an exclusion limit of about 5,000 Daltons, wherein the particle packed column has an interparticle volume and a volume of the applied extract is not greater than the interparticle volume; and
(v) after the applying of (iv), passing a buffer through the column, and collecting the DNA-compaction proteins in a peak corresponding to an excluded volume of the column, wherein the DNA-compaction proteins comprise one or more histone proteins.

2. The method of claim 1, wherein the organic cation is selected from the group consisting of guanidinium, ethacridine, methylene blue, daunomycin, doxorubicin, chlorhexidine, alexidine, benzalkonium chloride, tris(2-aminoethyl) amine, cetyltrimethylammonium, polyethyleneimine and combinations thereof.

3. The method of claim 2, wherein a concentration of the ethacridine or the methylene blue is in a range selected from the group consisting of a non-zero amount to 0.05% (weight to volume), 0.01 to 0.1%, 0.02 to 0.05%, and 0.03 to 0.10%.

4. The method of claim 2, wherein the concentration of the guanidinium is in a range selected from the group consisting of 0.5 to 1.5 M, 0.8 to 1.2 M, and 0.9 to 1.1 M.

5. The method of claim 1, wherein the neutral salt is present in a concentration range from about 1 M to about 3 M.

6. The method of claim 1 or 5, wherein the neutral salt is sodium chloride or potassium chloride.

7. The method of claim 1, wherein the nonionic surfactant is selected from the group consisting of Tween 20, Tween, 40, Tween 60, and Nonidet NP40.

8. The method of claim 1 or 7, wherein the nonionic surfactant is present in a concentration range from about 0.05% to about 0.25% w/v.

9. The method of claim 1, wherein the preparation is selected from the group consisting of a cell culture supernatant, a bodily fluid, a tissue homogenate, and a fraction from a fractionating process.

10. A kit configured to perform the method of claim 1 comprising: an organic cation, a neutral salt, a nonionic surfactant, an acid at a pH of about 0.1 to about 1.0, a column, electropositive particles suitable for practicing anion exchange chromatography, and a buffer.

11. The kit of claim 10, wherein the organic cation comprises ethacridine or methylene blue, the nonionic surfactant is selected from the group consisting of polyethylene glycol sorbitan monolaurate, polyoxyethylenesorbitan monopalmitate, polyethylene glycol sorbitan monostearate, and octylphenoxypolyethoxyethanol, and the neutral salt is sodium chloride or potassium chloride.

12. The method of claim 1, wherein the particle packed column comprises electropositive particles suitable for practicing anion exchange chromatography in void exclusion mode.

* * * * *